United States Patent
Stoltz

(10) Patent No.: US 6,296,859 B1
(45) Date of Patent: Oct. 2, 2001

(54) SYNERGISTIC COMPOSITION COMPRISING A COMPOUND OF LIPOAMINO ACID STRUCTURE AND A WATER LILY EXTRACT

(75) Inventor: Corinne Stoltz, Paris (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 0 days.

(21) Appl. No.: 09/263,091

(22) Filed: Mar. 5, 1999

(30) Foreign Application Priority Data

Mar. 9, 1998 (FR) .................................................. 98 02828

(51) Int. Cl.$^7$ ...................................................... A61K 7/48
(52) U.S. Cl. ........................ 424/401; 424/195.1; 514/559; 514/740
(58) Field of Search ................................. 424/401, 195.1; 514/559, 740

(56) References Cited

U.S. PATENT DOCUMENTS 5,458,881 * 10/1995 Berger et al. ........................ 424/401
5,925,348 * 7/1999 Riley et al. .

FOREIGN PATENT DOCUMENTS

| 62 051606 | 3/1987 | (JP) . |
|---|---|---|
| 01047708 | * 2/1989 | (JP) . |
| 09 255518 | 9/1997 | (JP) . |
| 11071234 | * 3/1999 | (JP) . |
| WO 92/21318 | 12/1992 | (WO) . |

* cited by examiner

*Primary Examiner*—Michael A. Williamson
(74) *Attorney, Agent, or Firm*—Young & Thompson

(57) ABSTRACT

Composition characterized in that it comprises, as active principle, at least one compound of formula (I):

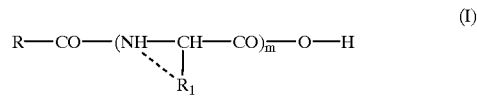

its topically acceptable salts, which R represents the characterizing chain of a saturated or unsaturated, linear or branched fatty acid containing from 3 to 30 carbon atoms, $R_1$ represents the characterizing chain of an amino acid and m is between 1 and 5, and the constituents of at least one extract and/or of at least one tincture from plants of the Nympheacea family. The composition is useful in cosmetics.

14 Claims, No Drawings

SYNERGISTIC COMPOSITION COMPRISING A COMPOUND OF LIPOAMINO ACID STRUCTURE AND A WATER LILY EXTRACT

FIELD OF THE INVENTION

The present invention relates to a novel cosmetic composition for compounds with a lipoamino acid structure and with calmant activity.

BACKGROUND OF THE INVENTION

In modern life, skin is attacked by various factors outside the human body; these are, in particular, atmospheric pollution, ultraviolet radiation, either of natural or artificial nature, or other stresses such as mechanical or chemical stresses.

On account of the ever-increasing occurrence of these problems, in particular in highly urbanized areas, skin protection has become a predominant aspect of the search for novel cosmetic products. In response to attack or to sensations of attack on the skin, the concept of a calmant cosmetic product has been developed.

According to European Economic Community counsel directive No. 76/768/EEC of Jul. 27, 1976 modified by directive No. 93/35/EEC of Jun. 14, 1993, the term "cosmetic product" refers to any substance or preparation intended to be placed in contact with the various surface parts of the human body (epidermis, pilous and hair system, nails, lips and genital organs) or with the teeth and the oral mucosae in order, exclusively or mainly, to clean them, fragrance them, modify their appearance and/or correct body odours and/or protect them or keep them in good condition.

In general, the term "calmant product or calmant cosmetic formulation" refers to any product in formulation which gives a sensation of well-being of the skin, whether this is, in particular, a sensation of softness, of elasticity and/or of comfort experienced by the individual by applying the product to his or her skin.

The Applicant has discovered that all of these stresses on the skin induce a pre-inflammatory state.

During this state, various events occur, in particular the production of free radicals and the synthesis of various pro-inflammatory enzymes, such as elastase. These two phenomena (production of free radicals and of elastase) will not only maintain and propagate this state of inflammation, but will also have harmful consequences on the skin. The production of free radicals, for example, is responsible for the death of many cells, on account of the deleterious effects induced in particular in primordial molecules such as DNA, lipids or proteins; as for elastase, it degrades elastin, the main protein in dermal support. These two phenomena will thus reflect the events which occur during an inflammation, as well as the harmful effects on the skin resulting therefrom.

The Applicant has thus sought to develop a composition which is effective, on the one hand, against the cutaneous stress caused by external attacking factors on the skin, in particular against the harmful effects caused by enzymes which maintain and develop the inflammatory process, and, on the other hand, by inhibiting the process for the production of free radicals.

Compounds of lipoamino acid structure, such as, for example, those described in the international patent applications published under Nos. WO 92/20647, WO 92/21318, WO 94/26694 and WO 94/27561 are, on account of their amphiphilic structure, biological vectors which are particularly advantageous as regulators of skin physiology and prove to be suitable for a large number of applications, in particular in cosmetics.

SUMMARY OF THE INVENTION

Now, the Applicant has found that compositions comprising, as active principles, a combination of lipoamino acids with certain natural extracts of plants, have both anti-free-radical activity and anti-elastase activity. The Applicant has also found that this activity is the result of the synergism between these two families of active principles.

One subject of the invention is a composition characterized in that it comprises, as active principle, at least one compound of formula (I):

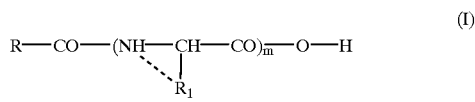

or its topically acceptable salts, in which R represents the characterizing chain of a saturated or unsaturated, linear or branched fatty acid containing from 3 to 30 carbon atoms, $R_1$ represents the characterizing chain of an amino acid and m is between 1 and 5,
and the constituents of at least one extract and/or of at least one tincture from plants of the Nympheacea family.

The expression "topically acceptable salt" refers to any salt of the acid of formula (I) which is biologically acceptable for the skin and/or the mucosae, i.e. any salt which can, in particular, adjust the pH of the composition to a value of between 3 and 8 and preferably approximately equal to 5, i.e. to a pH in the region of the skin's pH. These may be, in particular, alkali metal salts such as the sodium, potassium or lithium salts, alkaline-earth metal salts such as the calcium, magnesium or strontium salts; they may also be metal salts such as the divalent zinc or manganese salts or alternatively the trivalent iron, lanthanum, cerium or aluminum salts.

The compound of formula (I) present in the composition which is the subject of the present invention can be in free acid form or in partially or totally salified form.

The expression "characterizing chain" used in the context of the present patent application denotes the main non-functional chain of the fatty acid or of the amino acid under consideration.

Thus, for a fatty acid corresponding to the general formula R—COOH, the characterizing chain will be the chain represented by R. The radical R represents in particular a radical containing from 5 to 22 carbon atoms chosen from the pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl, docosenyl or heptadecadienyl or decenyl radicals. The invention relates more particularly to the composition as described above for which, in formula (I), the fragment R—CO contains from 7 to 22 carbon atoms and represents in particular one of the following radicals: hexanoyl, heptanoyl, octanoyl (capryloyl), decanoyl (caproyl), undecylenoyl, dodecanoyl (lauroyl), tetradecanoyl (myristyl), hexadecanoyl (palmitoyl), octadecanoyl (stearyl), eicosanoyl (arachidoyl), docosanoyl (behenoyl), octadecenoyl (oleyl), eicosenoyl (gadoloyl), docosenoyl (erucyl), octadecadienoyl (linolenoyl). In a first preferred variant of the present invention, in formula (I), the fragment R—CO (I) contains from 14 to 18 carbon atoms.

For an amino acid represented by the general formula $$H_2N-CHR_1-COOH,$$

as for an amino acid represented by the formula:

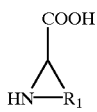

the characterizing chain will be the chain represented by $R_1$. $R_1$ represents in particular the characterizing chain of one of the amino acids chosen from glycine, alanine, serine, aspartic acid, glutamic acid, valine, threonine, arginine, lysine, proline, leucine, phenylalanine, isoleucine, histidine, tyrosine, tryptophan, asparagine, cysteine, cystine, methionine, hydroxyproline, hydroxylysine and ornithine.

The invention relates more particularly to the composition as described above for which, in formula (I), $R_1$ represents the characterizing chain of proline.

The expression "at least one compound of formula (I)" means that the composition according to the invention can contain one or more of these compounds.

In the definition of the composition which is the subject of the present invention, the words "extract" and "tincture" are used in their respective senses as established in the 1997 edition of the European Pharmacopoeia; extracts are concentrated preparations of liquid, solid or intermediate consistency, generally obtained from dried plant or animal starting materials. Tinctures are preparations generally obtained from dried plant or animal starting materials.

The expression "extracts or tinctures from plants of the Nympheacea family" denotes in particular the extracts or tinctures of water lily, such as "*Nuphar japonicum*", of lotus, such as "*Nelumbo nucifera*" or of "*Brasenia purpurea*". These extracts or tinctures are commercially available. Some are listed in the French and/or European Pharmacopoeias. The invention relates more particularly to the composition as described above in which the extract or tincture from plants of the Nympheacea family is an extract of water lily and, more particularly, an extract of water lily flower.

DETAILED DESCRIPTION OF THE INVENTION

The compounds of formula (I) are generally obtained by acylation of compounds of formula (I')

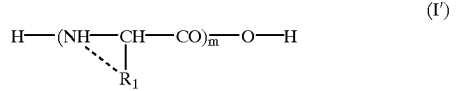

or of their salts, which are themselves obtained by total or partial hydrolysis of proteins of all origins. These proteins can be of animal origin, such as, for example, collagen, elastin, fish flesh protein, fish gelatin, keratin or casein, of plant origin, such as proteins from cereals, from flowers or from fruit, such as, for example, proteins obtained from soybean, from sunflower, from oat, from wheat, from corn, from barley, from potato, from lupin, from horsebean, from sweet almond, from kiwi, from mango or from apple; they can also be proteins obtained from chorellae (unicellular algae), from pink algae, from yeasts or from silk. This hydrolysis can be carried out, for example, by heating, to temperatures of between 60 and 130° C., of a protein placed in an acidic or alkaline medium. This hydrolysis can also be carried out enzymatically with a protease, optionally coupled with an alkaline or acidic post-hydrolysis.

When m is greater than 1, $R_1$ represents several of the characterizing chains of amino acids, depending on the hydrolysed protein and the degree of hydrolysis.

In a preferred variant of the present invention, when the composition comprises only one compound of formula (I), m is equal to 1, and when the composition comprises a mixture of compounds of formula (I), the average degree of condensation of the N-acylated amino acids in this mixture is less than 2.

The acylation reaction which gives the compounds of formula (I) mentioned above can be carried out chemically in alkaline medium (pH from 8 to 10) according to the Schotten-Baumann reaction, or enzymatically, and a person skilled in the art can refer in particular to the reference Surfactant Science Series, volume 7, Anionic Surfactants, part II, chapter 16, pages 581 to 617 (Marcel Dekker—1976). In general, the embodiment currently preferred for the preparation of the lipoamino acid compounds of formula (I) comprises the following steps:

a) Acylation in alkaline medium (pH 8 to 10) of an excess of a mixture of amino acids (mixed at the time of use or obtained by complete hydrolysis of a protein) with a fatty acid (or a mixture of fatty acids), in the form of the acid chloride or the anhydride. The amino acids/acid chloride ratio is preferably from 1.05 to 1.30 equivalents. The optimum acylation temperature is about 80° C. but varies from one amino acid to another between 60 and 110° C. The acylation time depends on the equipment used (size, stirring); it is about 2 hours for an acylated mass of 500 kg and about 5 hours for an acylated mass of 5000 kg.

b) Cleavage of the alkaline acylate by acidification in order to decant the water-soluble impurities and to release the acidic organic acylate (optimal pH of from 0.5 to 3 depending on the amino acids).

c) Purification by washing with water or with addition of electrolytes or of co-solvent in order to promote the decantation.

Besides the active principles, the composition according to the invention comprises inorganic or organic vehicles commonly used in the manufacture of compositions intended to be formulated as preparations for cosmetic and/or pharmaceutical use; mention may be made, for example, of water and polyols such as propylene glycol, dipropylene glycol, butylene glycol, hexylene glycol or glycerol.

In a preferred aspect of the present invention, the composition as described above comprises from 15% to 60%, and more particularly from 20% to 40%, by weight of at least one compound of formula (I) in which the fragment R—CO comprises from 8 to 18 carbon atoms, or its topically acceptable salts, and from 0.01% to 10% by weight, and more particularly from 0.01% to 5% by weight, of constituents of at least one extract and/or tincture from plants of the Nympheacea family.

According to the European Pharmacopoeia, the extracts can be in the form of fluid extracts, soft or firm extracts, or dry extracts. In the above definition of the composition according to the invention, the weight percentages of constituents of the extract or of the tincture correspond to the weight percentages of dry residue, the dry residue being obtained by evaporating the solvent and desiccating the extract or the tincture under operating conditions in which the constituents suffer minimal degradation.

The composition as defined above comprises in particular from 20% to 40% by weight of N-palmitoylproline and from 0.01% to 1% by weight of constituents of an extract of water lily, and more particularly of water lily flower. The composition according to the invention can also comprise from 0.1% to 10% by weight of magnesium potassium aspartate.

In another variant of the present invention, the composition as described above also comprises from 0.1% to 10% by weight of zinc gluconate.

The composition which is the subject of the present invention is prepared by methods which are known to those skilled in the art. In general, at least one extract and/or one tincture from plants is introduced, with stirring, into a composition comprising at least one compound of formula (I), this introduction being in an amount which is suitable to achieve the desired concentration of constituents of the extract and/or of the tincture in the final solution. If necessary, or if desired, the extract and/or the tincture are prediluted before mixing.

The composition according to the invention is used in cosmetics. As shown in the examples which follow, the composition according to the invention is characterized, unexpectedly, by an anti-elastase and anti-free-radical two-fold activity. This allows it to be used, in particular, for calming and/or protecting sensitive skin or for calming skin subjected to exposure to sunlight, for moisturizing dry skin, for slowing down the ageing of the skin and/or for treating skin with a tendency to develop acne; in this latter indication, the composition according to the invention can be used as a treatment complementary to the medical treatment of acne.

The composition according to the invention is also used during a simple act of body hygiene or during a treatment complementary to the medical treatment of an infection.

The composition according to the invention is also used in treating the scalp, in particular as an antidandruff active agent.

These uses also constitute in themselves a subject of the present invention.

Depending on the use, the composition as described above is used at different concentrations and in a formulation which is suitable for this use; such cosmetic compositions are usually in the form of aqueous solutions, dilute alcoholic solutions, or simple or multiple emulsions, such as water-in-oil (W/O), oil-in-water (O/W) or water-in-oil-in-water (W/O/W) emulsions in which the oils are of plant or mineral nature. Oils of mineral nature which may be mentioned are silicones. Cosmetic formulations which may be mentioned are creams, milks, tonic lotions or make-up-removing lotions, moist wipes, shower gels, foundations, soaps, liquid soaps, syndets, intimate hygiene products, shampoos, deodorants or make-up products.

Such formulations are known to those skilled in the art; their preparations are described, for example, in the patent applications published under Nos. WO 92/06778, WO 93/28204, WO 95/13863, WO 95/35089 or WO 96/22109.

One subject of the invention is thus also a cosmetic formulation which can be obtained by dilution from 1/10 to 1/20,000, preferably from 1/10 to 1/100, of the composition as described above, in one or more cosmetically acceptable excipients, and in particular a cosmetic formulation in the form of an oil-in-water emulsion having the appearance of a milk with a viscosity of less than 1 Pa.s, comprising, as emulsifier, a self-emulsifying composition based on fatty alcohols.

As preferred self-emulsifying compositions, mention may be made of Montanov™ 68, Montanov™ 14, Montanov™ 82 and Montanov™ 202 sold by the company SEPPIC.

Depending on the nature which can be given to the cosmetic formulation, it is possible, where appropriate, to add an inverted latex such as Sepigel™ 305, Sepigel™ 501 or Simulgel™ 600. The term "dilution" used hereinabove encompasses, in its widest sense, all of the steps which make it possible to pass from the composition as defined above to the cosmetic formulation intended to be sold. In another preferred embodiment of the present invention, the cosmetic formulation is a calmant cream or milk for treating sensitive skin, and particularly facial skin. In another preferred embodiment of the present invention, the cosmetic formulation is a moussing formula or a shampoo.

One subject of the invention is, particularly, a cosmetic composition comprising, as active principle, from 0.001% to 6% by weight of at least one compound of formula (I) and from 0.00005% to 1% by weight of constituents of at least one extract (II) and/or of at least one tincture from a plant of the Nympheacea family and, if desired, up to 1% of zinc gluconate.

One subject of the invention is, most particularly, a cosmetic formulation comprising, as active principle, from 0.1% to 2% by weight of palmitoylproline and from 0.0001% to 0.01% by weight of constituents of at least one extract of water lily, and more particularly of water lily flower.

Depending on the surface parts of the human body to which the cosmetic treatment used with the formulation as defined above is applied, and depending on the cosmetic treatment which is promoted for the said formulation, this formulation can contain, besides the synergistic composition which is the subject of the present invention, other active principles usually used in cosmetics.

The formulation as defined above can thus also contain one or more lipoamino acids in addition to those already initially contained in the composition which is the subject of the present invention. In one specific aspect of the above formulation, it also comprises from 0.1% to 1% by weight of undecylenoylglycine and/or from 0.1% to 1% by weight of octanoylglycine.

The examples which follow illustrate the invention without, however, limiting it.

EXAMPLE 1

A) Preparation of a composition according to the invention

A composition A was prepared comprising, as active principle, about 30% of palmitoylproline sodium salt and 0.1% of extract of water lily flower, from palmitoylproline and from a glycolic extract (butylene glycol) of water lily flower (*Nymphea alba*) sold by the company Alban Muller International; the pH of composition A is about 5.8.

B) Demonstration of the anti-elastase properties of the composition according to the invention a) Principle of the test:

It is known that human leukocytic elastase (HLE) is involved in a large number of inflammatory pathologies. This enzyme is capable, in particular, of degrading many macromolecules such as fibrous elastin, certain types of collagen, proteoglycans and glycoproteins. For this reason, human leukocytic elastase constitutes one of the links in the chain of reactions which accompany an inflammation phenomenon. Blocking this enzyme by an anti-elastase effect thus makes it possible to prevent the degradation of the abovementioned molecules and thus to inhibit the inflammation process. The anti-elastase properties of a given product can be demonstrated by means of an in-vitro test, carried out with a spectrophotometer, using a support substance which can be degraded and thus become coloured, on contact with human leukocytic elastase.

Such a substance can be, for example, N-methoxysuccinyl-alanine-proline-valine-para-nitroanilide, this normally colourless substance releasing, on hydrolysis with human leukocytic elastase, a coloured product, para-nitroaniline, whose formation kinetics can be monitored by spectrophotometry at 410 nm. The reaction is carried out in a spectrophotometer, thermostatically maintained at 25° C., fitted with a sample changer. All the kinetics are carried out at least three times, the average and the standard deviation then being calculated for the three values obtained. The presence of a molecule with anti-elastase activity is reflected by a limitation in the formation of the coloured product and the anti-elastase effect can then be calculated relative to a control curve obtained in the absence of the molecule. A correlation thus exists between the percentage of inhibition of the formation of the coloured product by the test compound and the percentage of inhibition of human leukocytic elastase. The percentage of inhibition thus calculated is also representative of the calmant activity of the test compound.

b) Results obtained

Composition A is diluted in water to give composition $A_1$, which has the following active principle concentrations:

|  | Palmitoylproline (% by weight of active material) | Extract of water lily flower (as ppm of active material) |
|---|---|---|
| $A_1$ | 0.001% | 0.03 ppm |
| $A_2$ | 0.0062% | 0.2 ppm |

The percentages of inhibition of the elastase are as follows:

| Product | Test concentration | % of anti-elastase inhibition |
|---|---|---|
| Palmitoylproline alone | 0.001% | 22% |
| Extract of water lily flower alone | 0.03 ppm | 28% |
| Palmitoylproline + Extract of water lily flower | 0.001% of palmitoylproline + 0.03 ppm of extract of water lily flower | 63% (additive effect = 50%) => synergism present |

These results show that at concentrations for which the palmitoylproline and the extract of water lily flower have a limited activity (22% and 28%), the combination of the two unexpectedly shows a higher activity (63% inhibition).

C) Demonstration of the anti-free-radical properties of the composition according to the invention.

a) Principle of the test

The determination of the anti-free-radical effect is based on the inhibition or the decrease in the rate of reduction of cytochrome C, by adding a test molecule to the reaction medium. The superoxide anion is generated by the action of xanthine oxidase on xanthine. In the absence of a molecule capable of capturing it, it results in the reduction of cytochrome C. The formation of reduced cytochrome C is monitored by a spectrophotometer, at 550 nm in the presence (Test) and in the absence (Control) of anti-free-radical molecules.

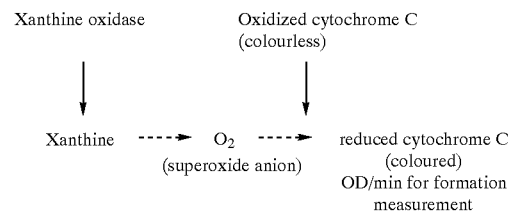

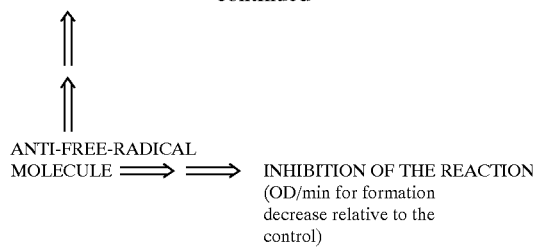

The reaction takes place in a spectrophotometer thermostatically adjusted to 25° C. and fitted with a sample changer. All of the kinetics are carried out at least three times; the average and the standard deviation are calculated for the three values obtained. A percentage of inhibition of the rate of formation of the coloured product (corresponding to the amount of free superoxide anion) will thus be calculated for each active agent tested. This calculation will be made relative to the rate of formation of the coloured product in the control (without active agent). The percentage of inhibition of the formation of the coloured product by the active agent will thus correspond to its percentage of inhibition of the superoxide anion.

b) Results obtained

| Product | Test concentration | % of anti-free-radical inhibition |
|---|---|---|
| Palmitoylproline alone | 0.0062% | 38% |
| Extract of water lily flower alone | 0.2 ppm | 20% |
| Palmitoylproline + Extract of water lily flower | 0.0062% of palmitoylproline + 0.2 ppm of extract of water lily flower | 74% (additive effect = 58%) => synergism present |

These results show a synergism of the anti-free-radical activity which is inherent to the combination of two products.

These tests show the advantage there is in combining, in the same formulation, a product of formula (I) and an extract of plants from the Nympheacea family.

EXAMPLES OF COSMETIC FORMULATIONS (EXAMPLES 2 TO 32)

EXAMPLE 2

Care Cream

| | |
|---|---|
| Cyclomethicone: | 10% |
| Composition A: | 3% |
| Sepigel ™ 501: | 0.8% |
| Montanov ™ 68: | 2% |
| Stearyl alcohol: | 1% |
| Stearic alcohol: | 0.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

(Montanov™ 68 (cetearyl glucoside) is a self-emulsifying composition as described in WO 92/06778, sold by the company SEPPIC)

(Sepigel™ 501 is a thickener based on acrylamide copolymers, sold by the company SEPPIC)

EXAMPLE 3
Care Cream

| | |
|---|---|
| Cyclomethicone: | 10% |
| Composition A: | 3% |
| Sepigel ™ 501: | 0.8% |
| Montanov ™ 68: | 2% |
| Perfluoropolymethyl isopropyl ether: | 0.5% |
| Stearyl alcohol: | 1% |
| Stearic alcohol: | 0.5% |
| Preserving agent: | 0.65% |
| Lysine: | 0.025% |
| EDTA (disodium salt): | 0.05% |
| Pemulen ™ TR: | 0.2% |
| Glycerol: | 3% |
| Water: | qs 100% |

(Pemulen™ TR is an acrylic polymer sold by Goodrich).

EXAMPLE 4
After-shave Balm

| | FORMULA | |
|---|---|---|
| A | Composition A: | 3% |
| | Sepigel ™ 501: | 1.5% |
| | Water: | qs. 100% |
| B | Micropearl ™ M 100: | 5.0% |
| | Sepicide ™ CI: | 0.50% |
| | Fragrance: | 0.20% |
| | 95° Ethanol: | 10.0% |

(Micropearl™ M 100 is an ultra-fine powder which feels very soft and gives a matt effect, sold by the company Matsumo)
(Sepicide™ CI, imidazolinurea, is a preserving agent sold by the company SEPPIC)
Procedure
Add B to A.

EXAMPLE 5
Satin Emulsion for the Body

| | FORMULA | |
|---|---|---|
| A | Simulsol ™ 165: | 5.0% |
| | Lanol ™ 1688: | 8.50% |
| | Karite butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Composition A: | 3% |
| | Sepigel ™ 501: | 3% |
| E | Sepicide ™ CI: | 0.3% |
| | Sepicide ™ HB: | 0.5% |
| | Monteine ™ CA: | 1% |
| | Fragrance: | 0.20% |
| | Vitamin E acetate: | 0.20% |
| | Sodium pyrrolidinonecarboxylate: | 1% (moisturizer) |

(Simulsol™ 165 (glyceryl stearate/PEG 100 stearate) is a self-emulsifying composition sold by the company SEPPIC)

(Lanol™ 1688 is an emollient ester with a non-greasy effect, sold by the company SEPPIC)
(Lanol™ 14M and Lanol™ S are consistency factors sold by the company SEPPIC)
(Sepicide™ HB (mixture of phenoxyethanol/methyl paraben/ethyl paraben/propyl paraben/butyl paraben) is a preserving agent sold by the company SEPPIC)
(Monteine™ CA is a moisturizer sold by the company SEPPIC)
Procedure
Add C to B, emulsify B in A at 70° C. and then add D at 60° C., followed by E at 30° C.

EXAMPLE 6
Body Milk

| | FORMULA | |
|---|---|---|
| A | Simulsol ™ 165: | 5.0% |
| | Lanol ™ 1688: | 12.0% |
| | Lanol ™ 14M: | 2.0% |
| | Cetyl alchol: | 0.3% |
| | Schercemol ™ OP: | 3% |
| B | Water: | qs 100% |
| C | Composition A: | 3% |
| | Sepigel ™ 501: | 0.35% |
| D | Sepicide ™ CI: | 0.2% |
| | Sepicide ™ HB: | 0.5% |
| | Fragrance: | 0.20% |

(Schercemol™ OP is an emollient ester with a non-greasy effect)
Procedure
Emulsify B in A at about 75° C.; add C at about 60° C., followed by D at about 30° C.

EXAMPLE 7
O/W Cream

| | FORMULA | |
|---|---|---|
| A | Simulsol ™ 165: | 5.0% |
| | Lanol ™ 1688: | 20.0% |
| | Lanol ™ P: | 1.0% (additive with stabilizing effect) |
| B | Water: | qs 100% |
| C | Composition A: | 3% |
| | Sepigel ™ 501: | 2.5% |
| D | Sepicide ™ CI: | 0.20% |
| | Sepicide ™ HB: | 0.30% |

(Lanol™ P is an additive with stabilizing effect, sold by the company SEPPIC)
Procedure
Introduce B into A at about 75° C.; add C at about 60° C., followed by D at about 45° C.

EXAMPLE 8
Non-greasy Antisun Gel

| | FORMULA | |
|---|---|---|
| A | Composition A: | 3% |
| | Sepigel ™ 501: | 0.8% |
| | Water: | 30% |

-continued

| | FORMULA | |
|---|---|---|
| B | Sepicide ™ CI: | 0.20% |
| | Sepicide ™ HB: | 0.30% |
| | Fragrance: | 0.10% |
| C | Colorant: | qs |
| | Water: | 30% |
| D | Micropearl ™ M 100: | 3.00% |
| | Water: | qs 100% |
| E | Silicone oil: | 2.0% |
| | Parsol ™ MCX: | 5.00% |

(Parsol™ MCX is octyl para-methoxycinnamate; it is sold by the company Givaudan)

Procedure
Introduce B into A; add C, then D, and then E.

EXAMPLE 9
Antisun Milk

| | FORMULA | |
|---|---|---|
| A | Sepiperl ™ N: | 3.0% |
| | Sesame oil: | 5.0% |
| | Parsol ™ MCX: | 5.0% |
| | λ carrageenan: | 0.10% |
| B | Water: | qs 100% |
| C | Composition A: | 3% |
| | Sepigel ™ 501: | 0.8% |
| D | Fragrance: | qs |
| | Preserving agent: | qs |

(Sepiperl™ N is a pearlescent agent sold by the company SEPPIC, based on a mixture of alkylpolyglucosides such as those described in WO 95/13863).

Procedure
Emulsify B in A at 75° C. and then add C at about 60° C., followed by D at about 30° C. and adjust the pH if necessary.

EXAMPLE 10
Massage Gel

| | FORMULA | |
|---|---|---|
| A | Composition A: | 3% |
| | Sepigel ™ 501: | 3.5% |
| | Water: | 20.0% |
| B | Colorant: | 2 drops/100 g |
| | Water: | qs |
| C | Alcohol: | 10% |
| | Menthol: | 0.10% |
| D | Silicone oil: | 5.0% |

Procedure
Add B to A; next, add C to the mixture, followed by D.

EXAMPLE 11
Care Gel for Massaging

| | FORMULA | |
|---|---|---|
| A | Composition A: | 3% |
| | Sepigel ™ 501: | 3.0% |
| | Water: | 30% |

-continued

| | FORMULA | |
|---|---|---|
| B | Sepicide ™ CI: | 0.20% |
| | Sepicide ™ HB: | 0.30% |
| | Fragrance: | 0.05% |
| C | Colorant: | qs |
| | Water: | qs 100% |
| D | Micropearl ™ SQL: | 5.00% |
| | Lanol ™ 1688: | 2% |

(Micropearl™ SQL is a mixture of microparticles containing squalane which is released under the action of massaging; it is sold by the company Matsumo)

Procedure
Prepare A; add B, then C and then D.

EXAMPLE 12
Radiant-effect Gel

| | FORMULA | |
|---|---|---|
| A | Composition A: | 3% |
| | Sepigel ™ 501: | 4% |
| | Water: | 30% |
| B | Elastin HPM: | 5.0% |
| C | Micropearl ™ M 100: | 3% |
| | Water: | 5% |
| D | Sepicide ™ CI: | 0.2% |
| | Sepicide ™ HB: | 0.3% |
| | Fragrance: | 0.06% |
| | Sodium pyrrolidinonecarboxylate | 50%:1% |
| | Water: | qs 100% |

Procedure
Prepare A; add B, then C and then D.

EXAMPLE 13
Body Milk

| | FORMULA | |
|---|---|---|
| A | Sepiperl ™ N: | 3.0% |
| | Glyceryl triheptonate: | 10.0% |
| B | Water: | qs 100% |
| C | Composition A: | 1.5% |
| | Sepigel ™ 501: | 1.0% |
| D | Fragrance: | qs |
| | Preserving agent: | qs |

Procedure
Melt A at about 75° C. Emulsify B in A at 75° C. and then add C at about 60° C., followed by D.

EXAMPLE 14
Make-up-removing Emulsion Containing Sweet Almond Oil

| | FORMULA | |
|---|---|---|
| | Montanov ™ 68: | 5% |
| | Sweet almond oil: | 5% |
| | Water: | qs 100% |
| | Composition A: | 1% |
| | Sepigel ™ 501: | 0.3% |
| | Glycerol: | 5% |

EXAMPLE 15

Moisturizing Cream for Greasy Skin

| FORMULA | |
|---|---|
| Montanov ™ 68: | 5% |
| Cetylstearyl octanoate: | 8% |
| Octyl palmitate: | 2% |
| Water: | qs 100% |
| Composition A: | 2% |
| Sepigel ™ 501: | 0.6% |
| Micropearl ™ M100: | 3.0% |
| Mucopolysaccharides: | 5% |
| Sepicide ™ HB: | 0.8 |
| Fragrance: | 0.3% |

EXAMPLE 16

Alcohol-free, Calmant After-shave Balm

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Sweet almond oil: | 0.5% |
| Water: | qs 100% |
| Composition A: | 3% |
| Sepigel ™ 501: | 3% |
| Sepicide ™ HB: | 0.3% |
| Sepicide ™ CI: | 0.2% |
| Fragrance: | 0.4% |

(Lanol™ 99 is isononyl isononanoate, sold by the company SEPPIC).

EXAMPLE 17

Cream Containing AHAs for Sensitive Skin

| FORMULA | |
|---|---|
| Lanol ™ 99: | 2% |
| Montanov ™ 68: | 5.0% |
| Water: | qs 100% |
| Composition A: | 0.1 to 5% |
| Sepigel ™ 501: | 1.5% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

-continued

| FORMULA | |
|---|---|
| Preserving agent: | 0.2% |
| Fragrance: | 0.3% |

EXAMPLE 18

After-sun Calmant Care

| FORMULA | |
|---|---|
| Lanol ™ 99: | 10.0% |
| Water: | qs 100% |
| Composition A: | 3% |
| Sepigel ™ 501: | 2.5% |
| Sepicide ™ HB: | 0.3% |
| Sepicide ™ CI: | 0.2% |
| Fragrance: | 0.4% |
| Colorant: | 0.03% |

EXAMPLE 19

Make-up-removing Milk

| FORMULA | |
|---|---|
| Sepiperl ™ N | 3% |
| Primol 352: | 8.0% |
| Sweet almond oil: | 2% |
| Water: | qs 100% |
| Composition A: | 2% |
| Sepigel ™ 501: | 0.8% |
| Preserving agent: | 0.2% |

EXAMPLE 20

Body Milk

| FORMULA | |
|---|---|
| Sepiperl ™ N | 3.5% |
| Lanol ™ 37T: | 8.0% |
| Solagum ™ L: | 0.05% |
| Water: | qs 100% |
| Benzophenone: | 2.0% |
| Dimethicone 350 cPs: | 0.05% |
| Composition A: | 2% |
| Sepigel ™ 501: | 0.8% |
| Preserving agent: | 0.2% |
| Fragrance: | 0.4% |

(Lanol™ 37T is glyceryl triheptanoate, sold by the company SEPPIC).
(Solagum™ L is a carrageenan sold by the company SEPPIC).

EXAMPLE 21

Fluid Emulsion of Alkaline PH

| FORMULA | |
|---|---|
| Marcol ™ 82: | 5.0% |
| NaOH: | 10.0% |
| Water: | qs 100% |
| Composition A: | 4% |
| Sepigel ™ 501: | 1.5% |

(Marcol ™ 82 is a liquid paraffin sold by the company ESSO).

EXAMPLE 22
Fluid Foundation

| FORMULA | |
|---|---|
| Simulsol ™ 165: | 5.0% |
| Lanol ™ 84D: | 8.0% |
| Lanol ™ 99: | 5.0% |
| Water: | qs 100% |
| Mineral fillers and pigments: | 10.0% |
| Composition A: | 3% |
| Sepigel ™ 501: | 1.2% |
| Preserving agent: | 0.2% |
| Fragrance: | 0.4% |

(Lanol™ 84D is dioctyl malate, sold by the company SEPPIC).

EXAMPLE 23
Antisun Milk

| FORMULA | |
|---|---|
| Sepiperl ™ N: | 3.5% |
| Lanol ™ 37T: | 10.0% |
| Parsol NOX ™: | 5.0% |
| Eusolex ™ 4360: | 2.0% |
| Water: | qs 100% |
| Composition A: | 3% |
| Sepigel ™ 501: | 1.8% |
| Preserving agent: | 0.2% |
| Fragrance: | 0.4% |

(Parsol NOX™ and Eusolex™ 4360 are two sunscreens sold, respectively, by the companies Givaudan and Merck).

EXAMPLE 24
Gel for Around the Eyes

| FORMULA | |
|---|---|
| Composition A: | 1% |
| Sepigel ™ 501: | 2% |
| Fragrance: | 0.06% |
| Sodium pyrrolidinonecarboxylate: | 0.2% |
| Dow Corning ™ 245 Fluid: | 2.0% |
| Water: | qs 100% |

(Dow Corning™ 245 Fluid is cyclomethicone, sold by the company Dow Corning).

EXAMPLE 25
Leave-in Care Composition

| FORMULA | |
|---|---|
| Composition A: | 3% |
| Sepigel ™ 501: | 1.5% |
| Fragrance: | qs |
| Preserving agent: | qs |
| Dow Corning ™ X2 8360: | 5.0% |
| Dow Corning ™ Q2 1401: | 15% |
| Water: | qs 100% |

(Dow Corning™ 245 Fluid is cyclomethicone, sold by the company Dow Corning).

EXAMPLE 26
Slimming Gel

| FORMULA | |
|---|---|
| Composition A: | 5% |
| Sepigel ™ 501: | 5% |
| Ethanol: | 30% |
| Menthol: | 0.1% |
| Caffeine: | 2.5% |
| Extract of butcher's-broom: | 2% |
| Extract of ivy: | 2% |
| Sepicide ™ HP: | 1% |
| Water: | qs 100% |

EXAMPLE 27
Soothing Cream for Sensitive Skin

| | |
|---|---|
| Composition A: | 3% |
| Sepigel ™ 305: | 1% |
| Montanov ™ 68: | 7% |
| Isostearyl isostearate: | 5% |
| Dimethicone: | 10% |
| Fragrance: | 2% |
| Sepicide ™ HB: | 0.3% |
| Sepicide ™ CI: | 0.2% |
| Water: | qs 100% |

EXAMPLE 28
Calmant Care Product

| | |
|---|---|
| Composition A: | 3% |
| Sepigel ™ 305: | 1.5% |
| Simulsol ™ 165: | 5% |
| Capric/caprilic triglyceride: | 5% |
| Sepicide ™ HB: | 0.3% |
| Sepicide ™ CI: | 0.2% |
| Fragrance: | 0.1% |
| Water: | qs 100% |

EXAMPLE 29
Cream-gel for Sensitive Skin

| | |
|---|---|
| Composition A: | 3% |
| Sepigel ™ 305: | 2% |
| Isohexadecane: | 5% |
| Borage oil: | 1% |
| Sepicide ™ HB: | 0.3% |
| Sepicide ™ CI: | 0.2% |
| Fragrance: | 0.05% |

EXAMPLE 30
After-sun Calmant Care Product

| | |
|---|---|
| Composition A: | 3% |
| Sepigel ™ 501: | 4% |
| Cyclomethicone and dimethiconol: | 5% |
| Lanol ™ 189: | 5% |
| Sepicide ™ HB: | 0.3% |
| Sepicide ™ CI: | 0.2% |

EXAMPLE 31

Calmant Gel for the Hands

| | |
|---|---|
| Composition A: | 3% |
| Sepigel ™ 305: | 4% |
| Isostearyl isostearate: | 5% |
| Micropearl ™ M305: | 1% |
| Glycerol: | 10% |
| Sepicide ™ HB: | 0.3% |
| Sepicide ™ CI: | 0.2% |
| Fragrance: | 0.2% |
| Water: | qs 100% |

(Micropearl™ M305 is a crosslinked copolymer of polymethyl methacrylate, sold by the company Matsumo).

EXAMPLE 32

Moisturizing Cream for Sensitive Skin

| | |
|---|---|
| Montanov ™ 202: | 3% |
| Phytosqualane: | 5% |
| Cyclomethicone: | 3% |
| Water: | qs 100% |
| Macadamia/kiwi oil: | 3% |
| Composition A: | 3% |
| Sepigel ™ 305: | 1% |
| Lipacide ™ C86: | 0.5% |
| Sepicide ™ HB: | 0.2% |
| Fragrance: | 0.05% |

(Montanov™ 202 (arachidyl glucoside/behenyl alcohol) is a self-emulsifying composition as described in WO 92/06778, sold by the company SEPPIC).
(Lipacide™ C8G (octanoylglycine) is sold by the company SEPPIC).

EXAMPLE 33

Self-tanning Care Product

| | |
|---|---|
| Composition A: | 3% |
| DHA: | 1% |
| Sepigel ™ 305: | 2% |
| Montanov ™ 202: | 3% |
| Sweet almond oil: | 7% |
| Dimethicone: | 3% |
| Fragrance: | 0.1% |
| Sepifilm ™ HB: | 0.3% |
| Sepifilm ™ CI: | 0.2% |
| Water: | qs 100% |

What is claimed is:

1. Composition which comprises, as active principle, from 15% to 60% by weight of at least one compound of formula (I):

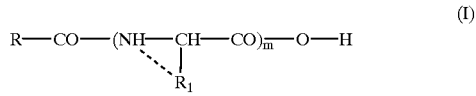

or its topically acceptable salts, in which R represents the characterizing chain of a saturated or unsaturated, linear or branched fatty acid containing from 3 to 30 carbon atoms, $R_1$ represents the characterizing chain of proline and m is between 1 and 5; and from 0.01% to 10% by weight of constituents of at least an extract of water lily flower.

2. Composition as defined in claim 1, which comprises from 20% to 40% by weight of at least one compound of formula (I) in which the fragment R—CO comprises from 8 to 18 carbon atoms, or its topically acceptable salts, and from 0.01% to 5% by weight of constituents of said extract of water lily flower.

3. Composition as defined in claim 2, which comprises from. 20% to 40% by weight of N-palmitoylproline and from 0.01% to 1% by weight of constituents of said extract of water lily flower.

4. Composition as defined in claim 1, which also comprises from 0.1% to 10% by weight of at least one of magnesium potassium aspartate and zinc gluconate.

5. Method for calming and/or protecting sensitive skin, which comprises applying to the skin an effective amount of the composition of claim 1 to calm and/or protect: the skin.

6. Method for moisturizing dry skin and/or slowing down the aging of the skin, which comprises applying to the skin an effective amount of the composition of claim 1 to moisturize or slow down the aging of the skin.

7. Cosmetic formulation which can be obtained by dilution from 1/10 to 1/20,000 of the composition as defined by claim 1, in one or more cosmetically acceptable excipients.

8. Cosmetic formulation according to claim 7, which is obtained by dilution from 1/10 to 1/100 of the composition as defined by claim 1, in one or more cosmetically acceptable excipients.

9. Formulation as defined in claim 7, in the form of an oil-in-water emulsion having the appearance of a milk with a viscosity of less than 1 Pa.s, comprising, as emulsifier, a self-emulsifying composition based on fatty alcohols.

10. Formulation as defined in claim 7, in the form of a calmant cream or milk for treating sensitive skin.

11. Formulation as defined in claim 7, in the form of a moussing formula or a shampoo.

12. Cosmetic formulation comprising, as active principle, from 0.001% to 6% by weight of at least one compound of formula (I):

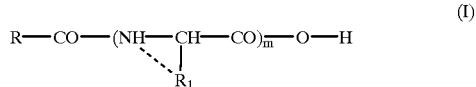

or its topically acceptable salts, in which R represents the characterizing chain of a saturated or unsaturated, linear or branched fatty acid containing from 3 to 30 carbon atoms, $R_1$ represents the characterizing chain of proline and m is between 1 and 5; and from 0.00005% to 1% by weight of constituents of an extract of water lily flower.

13. Cosmetic formulation as defined in claim 12, further comprising one or more compounds of lipoamino acid structure, and from 0.1% to 1% by weight of at least one of undecylenoylglycine and octanoylglycine.

14. Cosmetic formulation as defined in claim 12, wherein the active principle comprises from 0.1% to 2% by weight of palmitoylproline, and from 0.0001% to 0.01% by weight of the extract of water lily.

* * * * *